United States Patent
Steadham et al.

(10) Patent No.: US 7,331,933 B2
(45) Date of Patent: Feb. 19, 2008

(54) BALLOON CATHETER WITH A COMPRESSION MEMBER FOR BALLOON BONDING

(75) Inventors: Christopher L. Steadham, San Jose, CA (US); Christopher C. Pfaff, San Francisco, CA (US); Brett W. Cryer, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 19 days.

(21) Appl. No.: 10/335,481

(22) Filed: Dec. 31, 2002

(65) Prior Publication Data

US 2004/0127850 A1 Jul. 1, 2004

(51) Int. Cl.
*A61M 29/00* (2006.01)
(52) U.S. Cl. .................................. 604/96.01
(58) Field of Classification Search ............... 604/103, 604/96.01, 103.01, 265, 101.01–101.05, 604/523, 915, 916; 606/191–194
See application file for complete search history.

(56) References Cited

U.S. PATENT DOCUMENTS

| | | | |
|---|---|---|---|
| 3,746,003 A | 7/1973 | Blake et al. | |
| 4,130,119 A | 12/1978 | Sessions et al. | |
| 4,227,293 A | 10/1980 | Taylor | |
| 4,251,305 A * | 2/1981 | Becker et al. | 156/86 |
| 4,299,227 A | 11/1981 | Lincoff | |
| 5,100,386 A | 3/1992 | Inoue | |
| 5,195,969 A | 3/1993 | Wang et al. | |
| 5,308,354 A * | 5/1994 | Zacca et al. | 606/159 |
| 5,356,591 A * | 10/1994 | Pinchuk et al. | 264/573 |
| 5,501,759 A | 3/1996 | Forman | |
| 5,549,552 A * | 8/1996 | Peters et al. | 604/103.1 |
| 5,578,010 A | 11/1996 | Ashby | |
| 5,697,946 A * | 12/1997 | Hopper et al. | 606/185 |
| 5,868,704 A | 2/1999 | Campbell et al. | |
| 5,879,369 A | 3/1999 | Ishida | |
| 6,120,477 A | 9/2000 | Campbell et al. | |
| 6,364,894 B1 | 4/2002 | Healy et al. | |
| 6,500,147 B2 | 12/2002 | Omaleki et al. | |
| 6,723,113 B1 | 4/2004 | Shkolnik | |

* cited by examiner

*Primary Examiner*—Manuel Mendez
(74) *Attorney, Agent, or Firm*—Fulwider Patton LLP

(57) ABSTRACT

The present invention is directed to balloon catheter having a compression member securing one or more balloon skirts to the catheter shaft. The compression member may be a band or coil that sealing secures the balloon skirt to a catheter shaft. Metallic compression members may be swaged to compress the skirt against the shaft, and thus provide a uniform seal between the balloon skirt and the catheter shaft. The compression members are especially useful when the balloon is formed of a fluoropolymer, such as expanded polytetrafluoroethylene (ePTFE) or polyterafluoroethylene (PTFE).

16 Claims, 3 Drawing Sheets

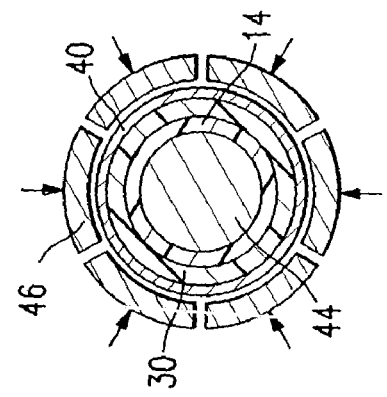
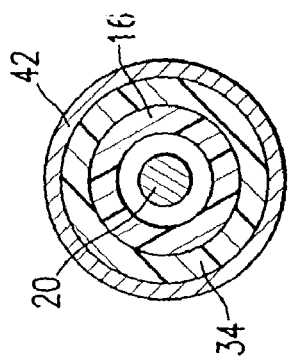
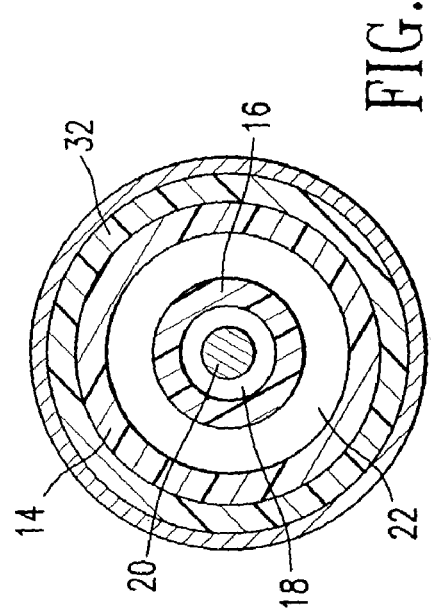
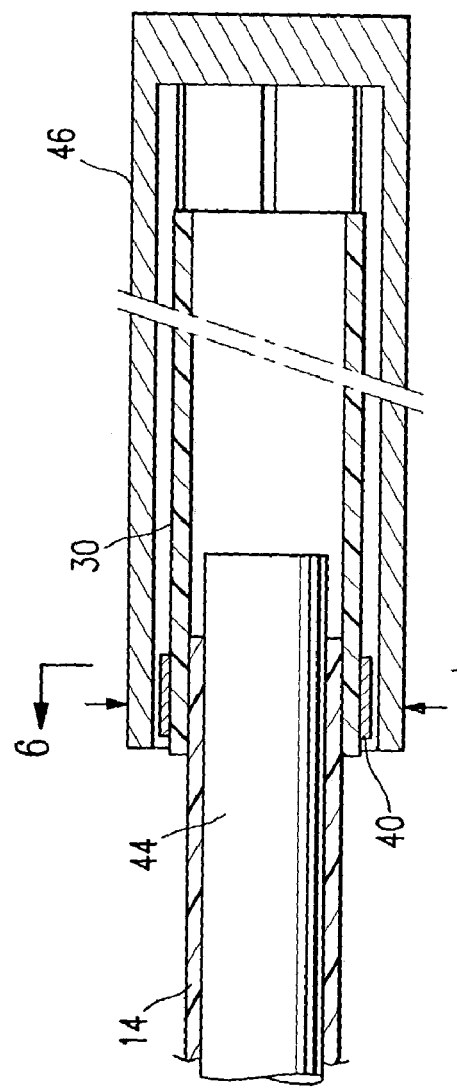

BALLOON CATHETER WITH A COMPRESSION MEMBER FOR BALLOON BONDING

BACKGROUND OF THE INVENTION

This invention generally relates to medical devices, and particularly intracorporeal devices for therapeutic or diagnostic uses, such as balloon catheters.

In percutaneous transluminal coronary angioplasty (PTCA) procedures, a guiding catheter is advanced until the distal tip of the guiding catheter is seated in the ostium of a desired coronary artery. A guidewire, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the manufacture of catheters, one difficulty has been the bonding of dissimilar materials together. The fusion bonding of a dissimilar material to a substrate material can be extremely difficult if the substrate has a low surface energy. For example, balloons formed of fluoropolymers such as expanded polytetrafluoroethylene (ePTFE) are not easily bonded to shafts without detrimentally effecting the ePTFE material. Specifically, one difficulty has been adhesively bonding ePTFE, absent some pretreatment causing decomposition of the fibril structure or the use of adhesives interlocking in the pore structure of the ePTFE. Chemical modification involving decomposition (i.e., defluoronation) of the ePTFE using compounds including bases (i.e., alkali metal compounds) such as sodium napthalide, or using plasma etching processes such as oxygen or trifluoroamine etching, have disadvantageous effects on the structural integrity of the ePTFE material. Additionally, lubricious materials such as high density polyethylene (HDPE) and polytetrafluoroethylene (PTFE), often used to form inner tubular members of catheters to provide good guidewire movement therein, have low surface energies of 31 dynes/cm and 18 dynes/cm, respectively, that make bonding to balloons formed of a dissimilar material such as a polyamide, e.g. PEBAX, difficult. Prior attempts to address this problem involved providing a multilayered shaft having an outer layer on the shaft configured to be bondable to the balloon. However, a decrease in shaft collapse pressure resistance may result in some cases when the outer layer has a lower stiffness than the shaft material. While adhesives may be used in some cases to bond dissimilar materials together, they are not ideal because they can increase stiffness of the component at the bond and some materials do not bond well to adhesives commonly used in medical devices.

It would be a significant advance to provide a balloon catheter with improved bonding of the balloon to the catheter shaft.

SUMMARY OF THE INVENTION

The present invention is directed to a balloon catheter having a compression member mounted about a balloon skirt section, securing the balloon skirt section to the catheter shaft. The compression member provides a low profile, a fluid tight seal, and is particularly advantageous when the balloon and/or shaft are fabricated from dissimilar materials or materials which are hard to bond.

A balloon catheter of the invention generally comprises an elongated shaft having a proximal section, a distal section, at least one lumen therein, and a balloon located on the distal section of the elongated shaft with an interior in fluid communication with the at least one lumen of the elongated shaft and having at least one skirt, and a compression member on the balloon skirt. In a presently preferred embodiment, the compression member is selected from a group consisting of a band and a coil.

In one embodiment, the compression member is swaged about the skirt section of the balloon in order to secure the balloon onto the catheter shaft, as well as provide a uniform seal around the entire circumference of the compression member. Swaging, as used herein, refers to the method of applying radially compressing force uniformly around the entire circumference of an object. Thus, unlike crimping in which a radially compressive force is applied at merely intermittent points around the circumference, a swaged member, such as a band of the present invention, provides a uniform seal at all points around the entire circumference of the swaged band. Consequently, the balloon is sealingly secured to the shaft in an improved manner around the entire circumference of the balloon skirt.

The compression member is mounted on at least one of the proximal or the distal skirt sections of the balloon. In a presently preferred embodiment, both the proximal and the distal skirt sections of the balloon have a compression member thereon securing both skirt sections to the shaft.

In one embodiment of the present invention, the compression member has an outer diameter around the circumference of the compression member which is not greater than an outer diameter of a first portion of the balloon skirt section directly adjacent to a second portion of the skirt section about which the compression member is mounted. Thus, the compression member compresses a part (i.e. second portion) of the skirt section so that the compression member outer diameter is equal to or less than the outer diameter of an adjacent part (i.e., first portion) of the balloon skirt section. Consequently, the compression member does not increase the profile of the catheter.

In one embodiment, the compression member, located on the skirt section of the balloon and sealingly securing the skirt section of the balloon to a portion of the distal section of the shaft, has an outer surface with a circumferential shape corresponding to a circumferential shape of an outer surface of the portion of the distal section of the shaft. Circumferential shape, as used herein, refers to the transverse cross-sectional shape extending around the entire circumference of the compression member's and the catheter shaft's outer surface. For example, in one embodiment, the outer surface of the catheter shaft has an overall circular transverse cross-section. Thus, the compression member having a corresponding circumferential shape would be of a similar circular shape around the entire circumference thereof and matching the shape of the circular shaft around the entire circumference thereof. The outer surface of the catheter shaft may, however, have a variety of suitable shapes, including oblong, triangular, elliptical, or rectangular, with a compression member having a similar corresponding circumferential shape.

A variety of suitable materials can be used to form the compression member of the invention including composite materials such as platinum-iridium, gold based alloys, stainless steel, platinum alloys, cobalt-chromium alloys, carbon fibers, polymeric materials such as nylon, polyamides, polyethelenes, polymides, polyester, shrink tubing or FEP, shape memory or superelastic materials such as nitinol, and radiopaque metals such as gold or tungsten, as wells as those materials previously mentioned. In addition to securing the balloon to the shaft, the compression members made from radiopaque materials are visible under fluoroscopy and thus can indicate the position of the balloon in a patient.

It should be noted that the features of the present invention and the compression members taught therein, can prove particularly useful with catheters having balloons formed of various fluoropolymers such as polytetrafluoroethylene (PTFE) or expanded polytetrafluoroethylene (ePTFE). As discussed above, it can be difficult to secure such balloons to a catheter shaft. The present invention, however, is not limited to use with catheters having fluoropolymer balloons. A variety of balloon materials can be used in the catheter of the present invention including material conventionally used in balloon catheter formation, particularly nylon polyether block amide (PEBAX), a nylon/PEBAX blend, polyamide, polyethylene (PE), high density polyethylene (HDPE), ultra-high density polyethylene (UHDPE), rubber (latex), polyisoprene, polyethylene terephthalate (PET), polyurethanes, and other hard to bond materials such as polypropylene and polyimide.

Additionally, the balloon catheter of the present invention has an improved fluid tight seal between the balloon and the shaft due to the compression member. The compression member provides a low profile, sealed portion and facilitates the securing of dissimilar or hard to bond materials together. These and other advantages of the invention will become more apparent from the following detailed description when taken in conjunction with the accompanying exemplary drawings.

BRIEF DESCRIPTION OF THE DRAWINGS

FIG. 3 is a transverse cross-section of the catheter shown in FIG. 1, taken along line 3-3.

FIG. 4 is a transverse cross-section of the catheter shown in FIG. 1, taken along line 4-4.

FIG. 5 is a longitudinal cross section of a swaging apparatus useful in a method that embodies features of the invention, in which a compression member comprising a band is swaged to a balloon skirt section disposed around a catheter shaft.

FIG. 6 is a transverse cross section of the swaging apparatus illustrated in FIG. 5, taken along line 6-6.

DETAILED DESCRIPTION OF THE INVENTION

Figure 1:
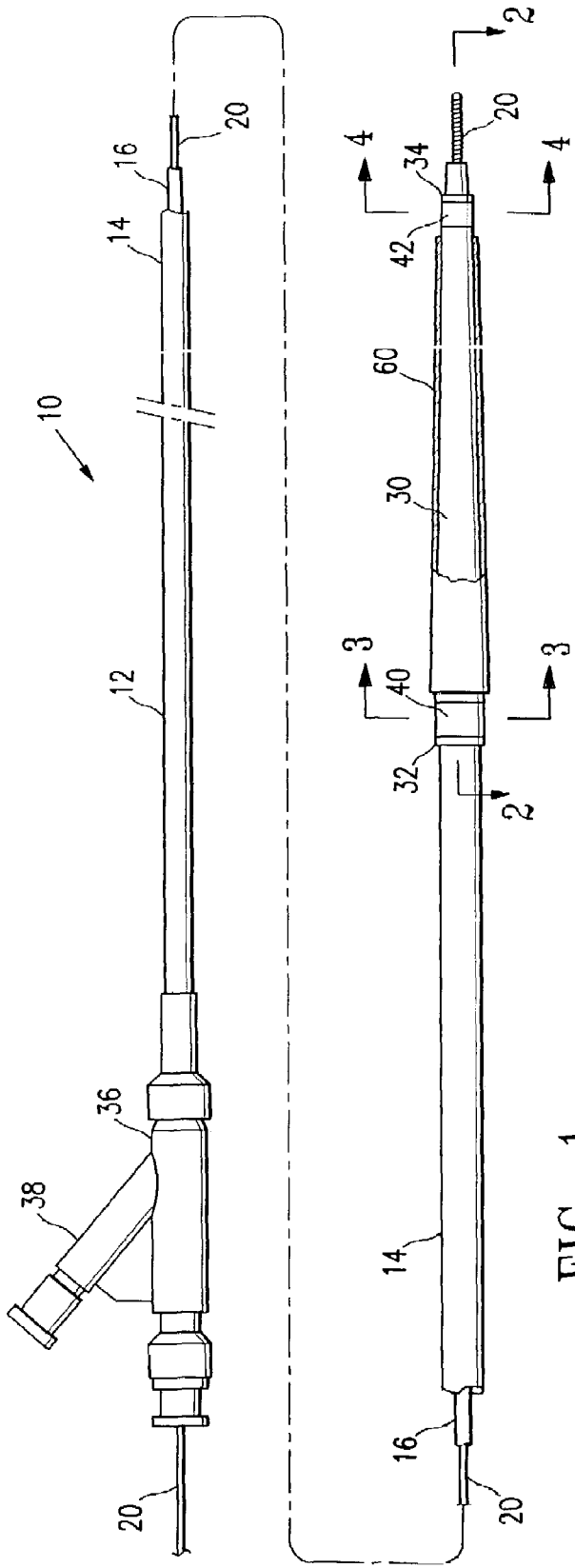
FIG. 1 is an elevational view, partially in section, of a balloon catheter that embodies features of the invention.
Figure 2:
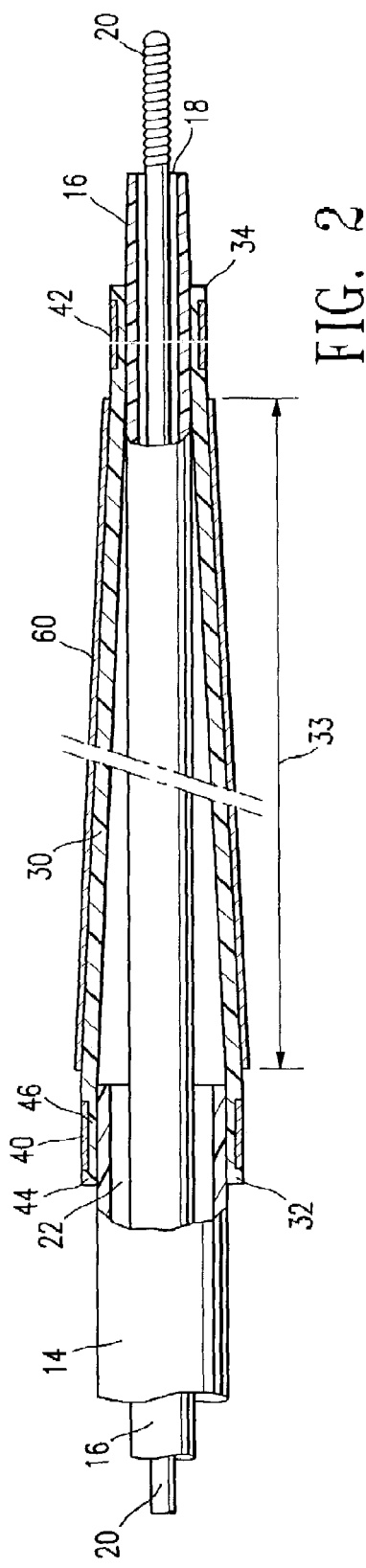
FIG. 2 is an enlarged, longitudinal cross section of a distal end of the catheter shown in FIG. 1.

FIGS. 1-4 illustrate a balloon catheter 10 embodying features of the present invention. The catheter 10 generally comprises an elongated catheter shaft 12 having an outer tubular member 14 and an inner tubular member 16. The inner tubular member 16 defines a guidewire lumen 18 configured to slidingly receive a guidewire 20, as best illustrated in FIG. 2 showing an enlarged longitudinal cross section of the distal end of the catheter illustrated in FIG. 1. The coaxial relationship between outer tubular member 14 and inner tubular member 16 defines an annular inflation lumen 22, as best illustrated in FIG. 3 showing a transverse cross section of the catheter of FIG. 1 taken along line 3-3.

An inflatable balloon 30 is disposed on a distal section of catheter shaft 12. The balloon 30 has a proximal skirt 32 sealingly secured to the distal end of outer tubular member 14 and a distal skirt 34 sealingly secured to the distal end of inner tubular member 16. The balloon interior is in fluid communication with the annular inflation lumen 22. An adapter 36 at the proximal end of catheter shaft 12 is configured to provide access to the guidewire lumen 18 and to direct inflation fluid through arm 38 into the inflation lumen 22. The balloon 30 has an inflatable working length 33 located between the skirt sections 32, 34 of the balloon 30 and a stent 60 mounted on the balloon 30 for implanting in a patient's body lumen. FIG. 1 illustrates the balloon 30 in an uninflated configuration. The distal end of catheter 10 may be advanced to a desired region of a patient's body lumen in a conventional manner and the balloon 30 inflated.

In the embodiment illustrated in FIG. 1, a proximal compression member 40 and a distal compression member 42 sealingly secure the balloon 30 to the outer tubular member 14 and the inner tubular member 16, respectively. The compression members 40, 42 are bands with a first outer diameter that allow the bands to be placed around an outer surface of the balloon and which contracts to a second, smaller diameter which then secures the balloon 30 to the shaft 12. In one embodiment, compression members 40, 42 are radiopaque marker bands. FIGS. 1 and 2 also illustrates an outer diameter around the circumference the compression members 40, 42 which is not greater than the outer diameter of a first portion 44 of the skirt section 32 directly adjacent to a second portion 46 of the skirt section about which the compression member is mounted. However, in an alternative embodiment, the compression members 40, 42 may have an outer diameter, which is greater than the outer diameter of the directly adjacent portion of the balloon.

FIGS. 3 and 4 illustrate the compression members 40, 42 having an outer surface with a circumferential shape corresponding to the circumferential shape of the outer surface of the portion of the catheter shaft onto which the compression member is mounted and secured. Although the circumferential shape of the compression members and the shaft is circular in the illustrated embodiments, a variety of suitable shapes can be alternatively used.

In a presently preferred embodiment, bands 40, 42 are formed of a super elastic material such as NiTi (Nitinol). The coils may also be formed from other types of materials commonly used in medical devices and that have a large thermal expansion coefficient.

FIG. 5 illustrates the method of swaging compression members 40, 42 onto a balloon skirt section to sealing secure the balloon 30 onto catheter shaft 12 with a mandrel 44 in place in the outer tubular member 14 for support. The compression member 40 is positioned on the outer surface of a balloon skirt. The assembly is then positioned in swaging apparatus 46, and the swaging apparatus 46 applies a radially compressive force uniformly around the entire circumference of the compression member. FIG. 6 illustrates a transverse cross section of the swaging apparatus 46 taken along line 6-6 in FIG. 5. The swaging apparatus 46 applies a radially compressive force uniformly around the entire circumference of the compression member 40. As a result of the uniform pressure applied by the swaging apparatus 46 to the compression member, a uniform seal is provided around all points around the entire circumference of the swaged member or band. Consequently, a balloon can be secured onto a catheter shaft in an improved manner around the entire circumference of the balloon skirt. A suitable commercially available swaging apparatus is model Torrington Model 100 available from Torrington, Swager & Vaille.

Figure 7:
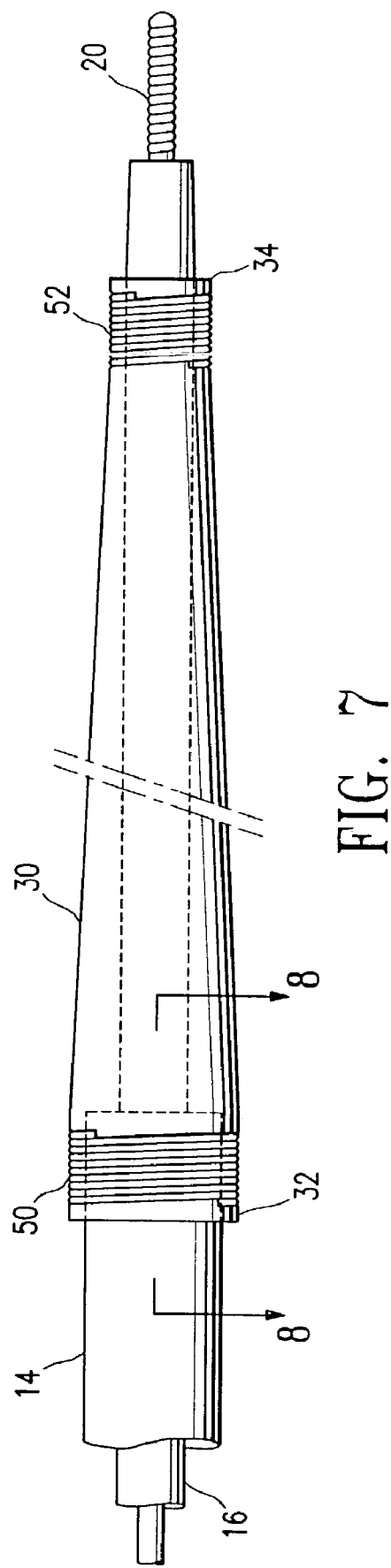
FIG. 7 is an enlarged, elevational view of the distal end of an alternative embodiment of a balloon catheter embodying features of the invention, having compression members comprising coils.
Figure 8:
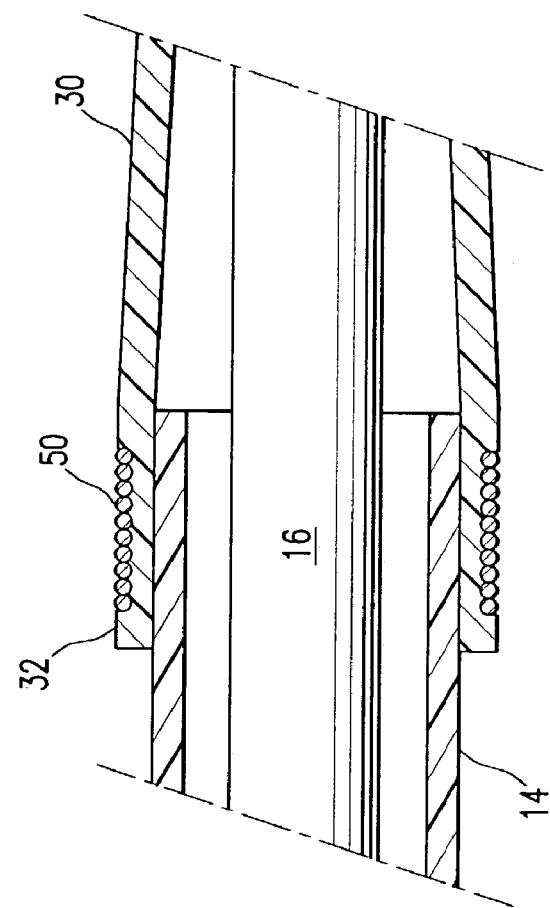
FIG. 8 is an enlarged longitudinal cross section of the balloon catheter shown in FIG. 7, taken along line 8-8.

FIGS. 7 and 8 illustrates another embodiment of the invention, having compression members 50 and 52 comprising coils securing the balloon 30 to the catheter shaft 12. Proximal compression member 50 secures the proximal skirt section 32 of the balloon to the distal end of the outer tubular member 14, and a distal compression member 52 on the distal skirt section 34 of the balloon sealingly secures the balloon 30 to a distal section of the inner tubular member 16.

FIG. 8 illustrates an enlarged longitudinal cross section of the catheter taken along line 8-8 at the proximal end of the balloon illustrated in FIG. 7. Similar to the embodiment of FIG. 1, compression members 50, 52 have an outer surface which has a circumferential shape that corresponds to the circular circumferential shape of the outer surface of the distal section of the shaft. The compression members 50, 52 can be contracted about the balloon skirt section 32, 34 by a variety of suitable methods such as swaging and heating to undergo a shape memory transition. In a presently preferred embodiment, the coils 50, 52 are formed of stainless steel or Nitinol. However, the coils can be made from any material commonly used in medical devices that has a large thermal expansion coefficient. In the embodiments illustrated in FIGS. 1 and 7, the balloon 30 is a wingless balloon which expands from low profile configuration which does not have deflated wings folded around the balloon circumference. In one embodiment, the balloon 30 is formed of ePTFE. Although for ease of illustration the balloon is shown as a single-layered balloon, balloon 30 formed of ePTFE would typically have a first layer formed of ePTFE, and a second layer formed of a different material such as an elastomeric polymer which limits or prevents leakage of inflation fluid through the porous ePTFE to allow for inflation of the balloon 30 and expands elastically to facilitate deflation of the balloon 30 to a low profile deflated configuration. The ePTFE layer is typically an outer layer and the elastomeric layer is typically an inner layer. While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter. However, one of skill in the art will readily recognize that other types of intravascular catheters may be used, such as and rapid exchange dilatation catheters having a distal guidewire port and a proximal guidewire port and a short guidewire lumen extending between the proximal and distal guidewire ports in a distal section of the catheter. Moreover, to the extent not otherwise described herein, the materials and methods of construction and the dimensions of conventional catheters may be employed with the catheter of the present invention. The features disclosed with one embodiment may be employed with other described embodiments as well. While the description of the invention is directed to embodiments for coronary applications, various modifications and improvements can be made to the invention without departing therefrom. Additionally, reference to the terms "members", "elements", "sections" and terms of similar import in the claims which follow shall not be interpreted to invoke the provisions of 35 U.S.C. §112, paragraph 6 unless reference is expressly made to the term "means" followed by an intended function.

What is claimed is:

1. A balloon catheter, comprising:
   a) an elongated shaft having a proximal end, a distal end, and at least one lumen;
   b) a balloon on a distal section of the elongated shaft having an uninflated configuration, an inflated configuration, an interior in fluid communication with the at least one lumen and having at least one skirt section, the skirt section having a circumference around which the skirt section is bonded to the shaft in the inflated and uninflated configurations; and
   c) a compression member fitted about a portion of the at least one skirt section so as to compress said skirt section against said elongated shaft such that the compression member has an outer diameter not greater than an outer diameter of said skirt section immediately adjacent to said compression member to secure the at least one balloon skirt section to a portion of the elongated shaft without said portion of the skirt section having a reduced inner diameter.

2. The catheter of claim 1 wherein the compression member is selected from a group consisting of a shape memory band, a super elastic band, a swaged band, and a coil.

3. The balloon catheter of claim 1 wherein the compression member is swaged about the skirt section of the balloon thereby providing a uniform seal around an entire circumference of the compression member.

4. The balloon catheter of claim 1 wherein the balloon has a proximal skirt section and a distal skirt section.

5. The balloon catheter of claim 4 wherein the compression member is a proximal compression member on the proximal skirt section of the balloon.

6. The balloon catheter of claim 4 wherein the compression member is a distal compression member on the distal skirt section of the balloon.

7. The catheter of claim 1 wherein the compression member is formed of a material selected from the group consisting of a metallic material, a polymeric material, and a radiopaque material.

8. The catheter of claim 1 wherein the compression member is a radiopaque marker.

9. The catheter of claim 1 wherein the balloon is formed of a fluoropolymer.

10. The catheter of claim 9 wherein the fluoropolymer is polytetrafluoroethylene or expanded polytetrafluoroethylene.

11. The catheter of claim 1 wherein the compression member has an outer surface with a circumferential shape corresponding to a circumferential shape of an outer surface of the portion of the distal shaft section.

12. A balloon catheter, comprising:
   a) an elongated shaft having a proximal end, a distal end, and at least one lumen;
   b) a balloon on a distal section of the elongated shaft, having an uninflated configuration, an inflated configuration, an interior in fluid communication with the at least one lumen, and a skirt section having a circumference around which the skirt section is sealingly secured to the shaft in the inflated and uninflated configurations; and
   c) an annular metallic band having an inner surface, an outer surface, and a uniform wall thickness from the band inner to the outer surface about an unreduced inner diameter portion of the skirt section of the balloon, sealingly securing the skirt section of the balloon to the distal shaft section, and having an outer diameter around a circumference of the band which is not greater than an outer diameter of a first portion of the skirt section directly adjacent to the portion of the skirt section about which the band is mounted.

13. The catheter of claim 12 wherein the compression member is swaged onto the skirt section of the balloon thereby providing a uniform seal around an entire circumference of the band.

14. The catheter of claim 12 wherein the balloon is formed of expanded polytetrafluoroethylene.

15. The catheter of claim 1 wherein the compression member has an inner surface, an outer surface, and a section which extends continuously around the entire circumference of the balloon skirt section and which has a maximum wall thickness from the inner to the outer surface which is uniform around the circumference.

16. The catheter of claim 12 wherein the band comprises a radiopaque material.

* * * * *